United States Patent [19]

Cho et al.

[11] Patent Number: 4,824,837

[45] Date of Patent: Apr. 25, 1989

[54] NOVEL 1,4-DIHYDROPYRIDINE DERIVATIVES, PROCESS FOR PREPARING THE SAME, AND AGENTS FOR TREATING DISORDERS OF CIRCULATORY SYSTEM

[75] Inventors: Hidetsura Cho; Masaru Ueda, both of Osaka, Japan

[73] Assignee: Suntory Limited, Osaka, Japan

[21] Appl. No.: 881,779

[22] Filed: Jul. 3, 1986

[30] Foreign Application Priority Data

Jul. 3, 1985 [JP] Japan ................................. 60-146290

[51] Int. Cl.[4] .................. A61K 31/455; C07D 211/86
[52] U.S. Cl. ..................................... 514/356; 514/336; 514/339; 514/255; 514/318; 546/284; 546/272; 546/194; 546/321; 546/263; 544/365; 544/131
[58] Field of Search ............... 546/321, 284, 272, 263, 546/194, 321; 514/356, 336, 339, 255, 318, 356; 544/365, 131

[56] References Cited

U.S. PATENT DOCUMENTS 3,974,275  8/1986  Bosset et al. ..................... 514/211
4,145,432  3/1979  Sato .................................... 546/321
4,423,052  12/1983  Araki et al. ......................... 546/321

FOREIGN PATENT DOCUMENTS 0039863 of 1981 European Pat. Off. .

Primary Examiner—Jane T. Fan
Attorney, Agent, or Firm—Cushman, Darby & Cushman

[57] ABSTRACT

1,4-Dihydropyridine derivatives of the formula (1):

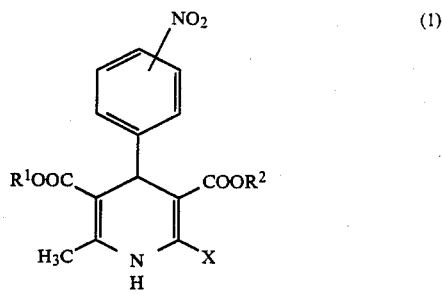

wherein X is a halogen; $R^1$ is a straight, branched or cyclic alkyl group having 1 to 10 carbon atoms, the group $-(CH_2)_n-Y$ [where n is an integer of 0 to 8, provided that n is an integer of 2 to 8 when Y is not bonded to COO— through carbon; Y is a cyclic alkyl group having 3-6 carbon atoms, an aryl group having 6-10 carbon atoms, a pyrrolidinyl group, an imidazolidinyl group, a thienyl group, a furyl group, an imidazolyl group, a pyridyl group, a pyrimidinyl group, a morpholinyl group, a thiomorpholinyl group or a pyrrolizidinyl group, the group

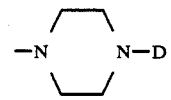

(where D is an aryl or aralkyl group having 6-15 carbon atoms which may be substituted by a halogenated alkyl group), or a 3-piperidinyl group substituted by a phenylalkyl group of 7-10 carbon atoms which may be substituted by one or two halogens], the group $-(CH_2)_m-O-Z$ (where m is an integer of 1 to 8; and Z is an alkyl or aryl group), or the group

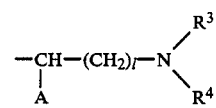

(where l is an integer of 1–7; A is a hydrogen atom, an alkyl group or an aryl group; and $R^3$ and $R^4$ which may be the same or different represent an alkyl, aryl or aralkyl group); and $R^2$ is a lower alkyl group, and pharmaceutically acceptable acid addition salts thereof are effective for treating disorders of the circulatory system and are useful as hypotensives, cerebral circulation improvers and antianginal agents.

Processes for producing the above copounds economically and effectively are also disclosed.

6 Claims, No Drawings

NOVEL 1,4-DIHYDROPYRIDINE DERIVATIVES, PROCESS FOR PREPARING THE SAME, AND AGENTS FOR TREATING DISORDERS OF CIRCULATORY SYSTEM

The present invention relates to novel 1,4-dihydropyridine derivatives of the formula (1):

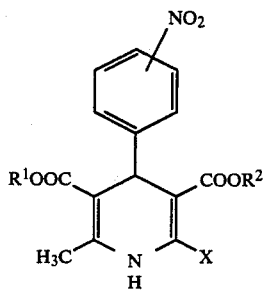

wherein X is a halogen; $R^1$ is a straight, branched or cyclic alkyl group having 1 to 10 carbon atoms, the group —$(CH_2)_n$—Y [where n is an integer of 0 to 8, provided that n is an integer of 2 to 8 when Y is bonded to COO— through the hetero atom; Y is a cyclic alkyl group having 3–6 carbon atoms, an aryl group having 6–10 carbon atoms, a pyrrolidinyl group, an imidazolidinyl group, a thienyl group, a furyl group, an imidazolyl group, a pyridyl group, a pyrimidinyl group, a morpholinyl group, a thiomorpholinyl group or a pyrrolizidinyl group, the group

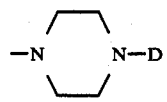

(where D is an aryl or aralkyl group having 6–15 carbon atoms which may be substituted by a halogenated alkyl group), or a 3-piperidinyl group substituted by a phenylalkyl group of 7–10 carbon atoms which may be substituted by one or two halogens], the group —$(CH_2)_m$—O—Z (where m is an integer of 1 to 8; and Z is an alkyl or aryl group), or the group

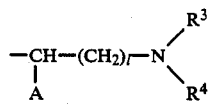

(where l is an integer of 1–7; A is a hydrogen atom, an alkyl group or an aryl group; and $R^3$ and $R^4$ which may be the same or different represent an alkyl, aryl or aralkyl group); and $R^2$ is a lower alkyl group. The present invention also relates to pharmaceutically acceptable acid addition salts of these 1,4-dihydropyridine derivatives, as well as a process for preparing such 1,4-dihydropyridine derivatives and pharmaceutically acceptable acid addition salts, and agents which contain them as effective ingredients for treating disorders of the circulatory system.

The novel 1,4-dihydropyridine derivatives of the formula (1) exhibit superior pharmacological effects such as hypotension, peripheral vasodilation, coronary vasodilation, cerebral vasodilation, and renovascular dilation over prolonged duration while causing only low levels of side effects. Because of these advantages, the 1,4-dihydropyridine derivatives of the formula (1) are useful as hypotensives, cerebral circulation improvers and antianginal agents.

Currently it is being found that calcium antagonists ($Ca^{++}$ antagonists), which had been spotlighted as new agents for treating disorders of the cardiovascular system, have a variety of pharmacological effects and are active not only against hypertension, angina pectoris, cerebral circulation disorder and arrhythmia but also in preventing arteriosclerosis and potentiating the effects of carcinostatic agents. Thus therapeutic uses of $Ca^{++}$ antagonists continue to increase.

$Ca^{++}$ antagonists which have been known include Nifedipine, Nicardipine, Verapamil, Diltiazem and the like.

Many studies have so far been made on Nifedipine and other dihydropyridine derivatives and they have been shown to exhibit interesting pharmacological actions such as vasodilation and hypotension. But there is room for improvement in the properties of these dihydropyridine derivatives such as duration of action, organ-selectivity, stability against light, heat, etc., and with respect to side effects.

The present inventors made concerted efforts in order to develop calcium antagonists with improvements made in the characteristics listed above. As a result, the inventors have found that the 1,4-dihydropyridine derivatives having the formula (1) shown above exhibit strong vasodilative action over prolonged duration with the utmost level of safety being ensured. The present invention has been accomplished on the basis of this finding.

In accordance with the present invention, the novel 1,4-dihydropyridine derivatives of the formula (1) and acid addition salts thereof are provided;

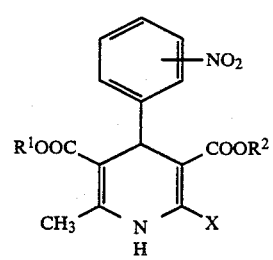

The 1,4-dihydropyridine derivatives of the formula (1) are synthesized through a route involving the formation of hydroxy-1,4-dihydropyridine derivatives of the following formula (4):

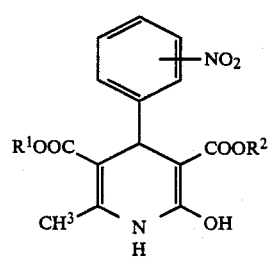

The hydroxy-1,4-dihydropyridine derivatives of formula (4) which are used as intermediate compounds in the process of the present invention may be synthesized by an improved version of the method described in C. F. H. Allen et al., Org. Syn. Coll., vol. 3, 377 (1955). According to this modified method, a dialkyl ester of malonic acid represented by formula (5):

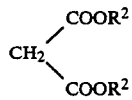
(5)

(where $R^2$ is the same as defined above) and one equivalent amount of nitrobenzaldehyde are heated in the presence of a base such as piperidine, methyl piperidine or trialkylamine to form a benzylidenemalonic acid ester derivative of the formula (2):

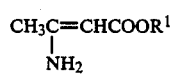
(2)

(where $R^2$ is the same as defined above). To this benzylidenemalonic acid ester derivative (2) is added one equivalent amount of a 3-aminocrotonic acid ester derivative of the formula (3):

$$CH_3C=CHCOOR^1$$
$$\quad\;\;|$$
$$\;\;NH_2$$
(3)

(where $R^1$ is the same as defined above) and the mixture is heated to form a benzylidene derivative of the formula (6):

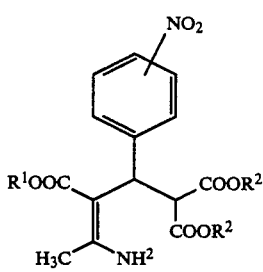
(6)

(where $R^1$ and $R^2$ are the same as defined above).

This benzylidene derivative (6) is heated either in the presence of a base such as triethylamine, potassium carbonate or potassium t-butoxide or, if $R^1$ has a basic group, in the absence of any base, thereby forming a hydroxydihydropyridine derivative having the formula (4):

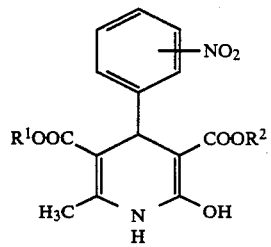
(4)

The compound of the present invention having the formula (1):

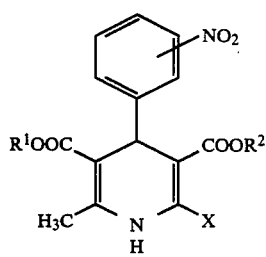
(1)

(where X, $R^1$ and $R^2$ are the same as defined above) may be obtained by heating said hydroxydihydropyridine derivative (4) in the presence of a halogenating agent such as phosphorus oxychloride or phosphorus pentachloride. Throughout the process of synthesizing this dihydropyridine derivative (1), an ether-, hydrocarbon- or amide-based solvent is desirably used, with the heating temperature being desirably selected at between 60° and 150° C.

The ester substituent $R^1$ at position 5 of the thus synthesized novel 1,4-dihydropyridine derivative (1) may be a straight, branched or cyclic alkyl group having 1–10 carbon atoms, the group —$(CH_2)_n$—Y [where n is an integer of 0 to 8, provided that n is an integer of 2 to 8 when Y is bonded to COO— through the hetero atom; Y is a cyclic alkyl group having 3–6 carbon atoms, an aryl group having 6–10 carbon atoms, a pyrrolidinyl group, an imidazolidinyl group, a thienyl group, a furyl group, an imidazolyl group, a pyridyl group, a pyrimidinyl group, a morpholinyl group, a thiomorpholinyl group or a pyrrolizidinyl group, the group

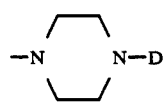

(where D is an aryl or aralkyl group having 6–15 carbon atoms which may be substituted by a halogenated alkyl group), or a 3-piperidinyl group substituted by a phenylalkyl group of 7–10 carbon atoms which may be substituted by one or two halogens], the group —$(CH_2)_m$—O—Z (where m is an integer of 1 to 8; and Z is an alkyl or aryl group), or the group

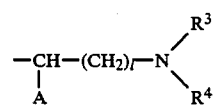

(where l is an integer of 1-7; A is a hydrogen atom, an alkyl group or an aryl group; and $R^3$ and $R^4$ which may be the same or different represent an alkyl, aryl or aralkyl group).

After the above reaction the products of the formula (1) of this invention can be purified by using conventional methods such as adsorption column chromatography, ion-exchange chromatography or recrystallization. Alternatively, the products can be treated with an inorganic acid such as hydrochloric acid, sulfuric acid or phosphoric acid, or an organic acid such as oxalic acid, succinic acid or malic acid to convert them to salts thereof, and then can be purified by recrystallization, adsorption chromatography or ion-exchange chromatography.

The thus prepared compounds (1) of the present invention exhibit a strong vasodilative effect in isolated guinea pig hearts, strong vasodilative and hypotensive effects in anesthetized dogs, and a strong hypotensive effect in conscious spontaneously hypertensive rats (SHR), and all of these effects last longer than in the case where existing drugs such as Nicardipine are administered.

Thus, the compounds of the present invention exhibit superior coronary vasodilative effects in guinea pigs and prove very effective in dogs for increasing the blood flow of vertebral artery, reducing the vascular resistance of vertebral artery and lowering the systemic blood pressure. Because of these effects, the compounds of the present invention will be useful in treating angina pectoris (myocardial infarction), disturbances of cerebral circulation, and hypertension.

The compounds (1) of the present invention can be administered alone or in combination with excipients in a variety of dosage forms such as tablets, troches, pills, granules, powders, capsules, ampules, suppositories and the like. The excipients include, for example, starch, dextrin, sucrose, lactose, silicic acid, carboxymethylcellulose, cellulose, gelatin, polyvinylpyrrolidone, glycerin, agar, calcium carbonate, sodium bicarbonate, paraffin, cetyl alcohol, stearic acid esters, kaolin, bentonite, talc, calcium stearate, magnecium stearate, polyethyleneglycol, water, ethanol, isopropylalcohol, propyleneglycol and the like.

For parenteral administration, the compounds of this invention are converted into water soluble salts thereof and the salts are dissolved in sterile distilled water or sterile physiological saline and are filled in ampules to be used for injection. If necessary, stabilizing agents and/or buffering agents can be included in the ampules.

For oral administration, the optimum dose range of the compound (1) of this invention is 5-500 mg per day for an adult. Of course, this dose range can be suitably changed depending upon the characteristics of the subjects including age, response, body weight, severity of disease etc.

The present invention can be illustrated by the following working examples and referential examples but it should be understood that it is not limited to them.

REFERENTIAL EXAMPLE A-a

2-Hydroxy-3,5-dimethoxycarbonyl-6-methyl-4-(3-nitrophenyl)-1,4-dihydropyridine [Compound (1)]

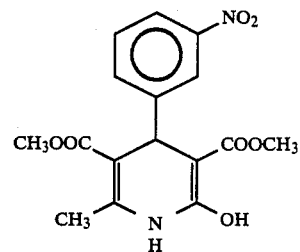

Methyl acetoacetate (5.0 g) was dissolved in methanol (20 ml) and after addition of a concentrated (28%) aqueous ammonia solution (5 ml), the mixture was heated under reflux for 16 hours. After completion of the reaction, the solvent was distilled off and the residue was subjected to extraction with chloroform, yielding 4.75 g (95.8%) of colorless needles. The needles (151 mg) and dimethyl 3-nitrobenzylidenemalonate (318 mg) were dissolved in anhydrous ethanol (13 ml) and the mixture was heated under reflux for 4.5 hours. The reaction mixture was cooled to room temperature to obtain 285 mg of crystals E. A portion (175 mg) of the crystals E was dissolved in 6 ml of anhydrous methanol and, after addition of triethylamine (1.5 ml), the mixture was heated under reflux for 16 hours. After the solvent was distilled off under reduced pressure, the residue was subjected to silica gel column chromatography (elution solvent: 2% chloroform/methanol) and the resulting crude crystals were recrystallized from a solution of chloroform/ether to obtain 152 mg (yield: 95.0%) of the desired compound (m.p. 150°-152° C.).

The following compounds were synthesized in accordance with the method of Referential Example A-a:

5-[2-(4-benzhydrylpiperazin-1-yl)ethyl]oxycarbonyl-2-hydroxy-3-methoxycarbonyl-6-methyl-4-(3-nitrophenyl)-1,4-dihydropyridine [Compound (3)];

5-[2-(N-benzyl-N-methylamino)ethyl]oxycarbonyl-2-hydroxy-3-methoxycarbonyl-6-methyl-4-(3-nitrophenyl)-1,4-dihydropyridine [Compound (4)];

5-[2-{4-(9-fluorenyl)piperazine-1-yl}ethyl]oxycarbonyl-2-hydroxy-3-methoxycarbonyl-6-methyl-4-(3-nitrophenyl)-1,4-dihydropyridine [Compound (5)];

2-hydroxy-3-methoxycarbonyl-6-methyl-4-(3-nitrophenyl)-5-(5-phenylpentyloxycarbonyl)-1,4-dihydropyridine [Compound (6)];

2-hydroxy-5-isopropoxycarbonyl-3-methoxycarbonyl-6-methyl-4-(3-nitrophenyl)-1,4-dihydropyridine [Compound (7)];

5-[1-(4-fluorobenzyl)-3-piperidyl]oxycarbonyl-2-hydroxy-3-methoxycarbonyl-6-methyl-4-(3-nitrophenyl)-1,4-dihydropyridine [Compound (8)];

5-n-heptyloxycarbonyl-2-hydroxy-3-methoxycarbonyl-6-methyl-4-(3-nitrophenyl)-1,4-dihydropyridine [Compound (9)];

2-hydroxy-3-methoxycarbonyl-6-methyl-4-(3-nitrophenyl)-5-(2-phenoxy)ethyloxycarbonyl-1,4-dihydropyridine [Compound (10)];

5-cyclopropylmethyloxycarbonyl-2-hydroxy-3-methoxycarbonyl-6-methyl-4-(3-nitrophenyl)-1,4-dihydropyridine [Compound (12)];

2-hydroxy-3-methoxycarbonyl-6-methyl-5-[2-(N-benzyl-N-methylamino)-1-phenylethyl]oxycarbonyl-4-(3-nitrophenyl)-3-methoxycarbonyl-1,4-dihydropyridine [Compound (13)];

2-hydroxy-3-methoxycarbonyl-5-(2-methoxyethyl)oxycarbonyl-6-methyl-4-(3-nitrophenyl)-1,4-dihydropyridine [Compound (14)]; and 2-hydroxy-3-methoxycarbonyl-6-methyl-4-(3-nitrophenyl)-5[2-(2-pyridyl)ethyl]oxycarbonyl-1,4-dihydropyridine [Compound (17)].

The physicochemical data of compound (1) and of the above-listed compounds are shown in Table A.

REFERENTIAL EXAMPLE A-b

2-Hydroxy-3,5-dimethoxycarbonyl-6-methyl-4-(3-nitrophenyl)-1,4-dihydropyridine [Compound (1)]

Crystals E (1.33 g) obtained during synthesis according to Referential Example A-a were dissolved in 20 ml of anhydrous dimethylformamide. The resulting solution was added to 2.42 g of anhydrous potassium carbonate and the mixture was stirred at 80° C. for 2.5 hours. The reaction mixture was poured into ice water and subjected to extraction with ether. The extract was distilled off to obtain crude crystals. This crude crystals were recrystallized from chloroform-ether to obtain 1.10 g (91%) of the desired compound.

After reaction was performed in accordance with Referential Example A-b, the extract was distilled off and the residue was subjected to silica gel column chromatography (elution solvent: 1% chloroform/methanol) to thereby obtain 3-ethoxycarbonyl-2-hydroxy-6-methyl-5-[5-(morpholino)ethel]oxycarbonyl-4-(2-nitrophenyl)-1,4-dihydropyridine [Compound (15)].

The physicochemical data of this compound are shown in Table A.

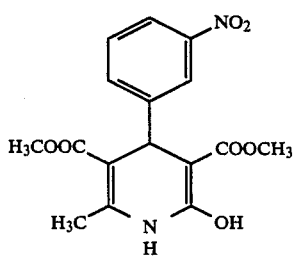

REFERENTIAL EXAMPLE B

2-Hydroxy-3-methoxycarbonyl-6-methyl-4-(3-nitrophenyl)-5-{2-(2-thienyl)ethoxycarbonyl}-1,4-dihydropyridine [Compound (11)]

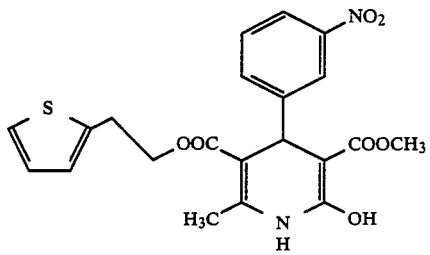

A mixture of 2-(2-thienyl)ethyl 3-amino-2-butenoate (1.8 g) and dimethyl 3-nitrobenzylidenemalonate (2.25 g) was dissolved in anhydrous 2-propanol (80 ml) and, after addition of triethylamine (27 ml), the mixture was refluxed for 21 hours. After the solvent was distilled off under reduced pressure, the residue was purified by thin-layer silica gel chromatography (developing solvent: chloroform/methanol=19/1; elution solvent: chloroform/acetone=2/1) so as to obtain 1.0 g (26%) of the desired compound.

The physicochemical data of this compound are shown in Table A.

REFERENTIAL EXAMPLE C

2-Hydroxy-3-methoxycarbonyl-6-methyl-4-(3-nitrophenyl)-5-(8-pyrrolizidinyl)methoxycarbonyl-1,4-dihydropyridine [Compound (16)]

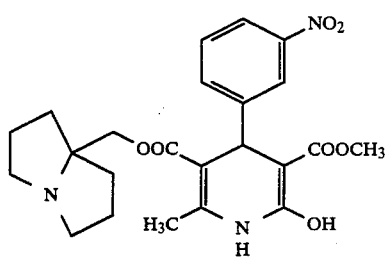

A mixture of 2-pyrrolizidinylmethyl 3-amino-2-butenoate (0.19 g) and dimethyl 3-nitrobenzylidenemalonate (0.23 g) was dissolved in 15 ml of anhydrous 2-propanol, and the mixture was heated under reflux for 22 hours. After the solvent was distilled off under reduced pressure, the residue was subjected to silica gel column chromatography (elution solvent: 5% chloroform/methanol), thereby obtaining 0.32 g (82.1%) of the desired compound.

By repeating the method of Referential Example C, 3,5-dimethoxycarbonyl-2-hydroxy-6-methyl-4-(2-nitrophenyl)-1,4-dihydropyridine [Compound (2)] was obtained.

The physicochemical data of the Compounds (16) and (2) are shown in Table A.

TABLE A

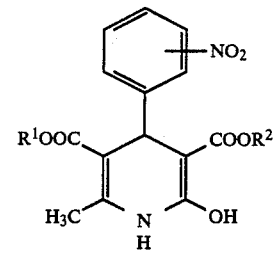

| Compound No. (Ref. Ex. No. showing method of synthesis) | Compound (position of nitro group) | Yield (%) | Description | IR Spectrum (cm$^{-1}$) as measured in CHCl$_3$ | NMR Spectrum (CDCl$_3$, δ ppm, 270 MHz) | High-resolution mass spectrum |
|---|---|---|---|---|---|---|
| 1 (A-a A-b) | (3-nitro group) R$^1$ = methyl group R$^2$ = methyl group | 95 (A-a) 91 (A-b) | mp 150–152° (chloroform/ether) pale yellow crystals | 3390 1740 1705 | 2.47(3H,s), 3.59(1H,s), 3.66(3H,s), 3.81(3H,s), 4.79(1H,s), 7.47–8.13(4H,m) | C$_{16}$H$_{16}$N$_2$O$_7$ cal'd: 348.3140 found: 348.3138 |
| 2 (C) | (2-nitro group) R$^1$ = methyl group R$^2$ = methyl group | 24 | mp 180–184° (chloroform/ n-hexane) pale yellow crystals | 3400 1740 1710 | 2.48(3H,s), 3.56(3H,s) 3.82(3H,s), 3.85(1H,s), 5.18(1H,s), 7.21–7.92(4H,m) | C$_{16}$H$_{16}$N$_2$O$_7$ cal'd: 348.3140 found: 348.3142 |
| 3 (A-a) | (3-nitro group) R$^1$ = 2-(4-benzhydryl-1-piperazinyl)ethyl group R$^2$ = methyl group | 94 | colorless powder | 3390 1740 1710 | 2.2–2.6(3H,m), 2.46(3H,s), 2.52(2H,t,J=6Hz), 3.56(1H,s), 3.77(3H,s), 4.14(1H,s), 4.2–4.3(2H,m), 4.76(1H,s), 7.1–8.1(14H,m) | C$_{34}$H$_{36}$N$_4$O$_7$ cal'd: 612.6861 found: 612.6866 |
| 4 (A-a) | (3-nitro group) R$^1$ = 2-(N—benzyl-N—methylamino)ethyl group R$^2$ = methyl group | 62 | pale yellow oil | 3395 1740 1710 | 2.12(3H,s), 2.44(3H,s), 2.58(2H,t,J=6Hz), 3.42(2H,s), 3.60(1H,s), 3.79(3H,s), 4.20(2H,t,J=6Hz), 4.80(1H,s), 7.2–8.1(9H,m), 8.72(1H,s) | C$_{25}$H$_{27}$N$_3$O$_7$ cal'd: 481.5080 found: 481.5081 |
| 5 (A-a) | (3-nitro group) R$^1$ = 2-[4-(9-fluorenyl)-1-piperazinyl]ethyl group R$^2$ = methyl group | 79 | pale yellow powder | 3390 1740 1710 | 2.2–2.65(10H,m), 2.44(3H,s), 3.55(1H,s), 3.75(3H,s), 4.1–4.25(2H,m), 4.74(1H,s), 4.80(1H,s), 7.2–8.2(12H,m) | C$_{34}$H$_{34}$N$_4$O$_7$ cal'd: 610.6703 found: 610.6701 |
| 6 (A-a) | (3-nitro group) R$^1$ = 5-phenylpentyl group R$^2$ = methyl group | 41 | pale yellow oil | 3400 1720 1710 | 1.30–1.75(6H,m), 2.45(3H,s), 2.52(2H,t,J=7Hz), 3.80(3H,s), 4.05(2H,t,J=7Hz), 4.77(1H,s), 7.10–8.20(9H,m) | C$_{36}$H$_{38}$N$_2$O$_7$ cal'd: 480.5203 found: 480.5219 |
| 7 (A-a) | (3-nitro group) R$^1$ = isopropyl group R$^2$ = methyl group | 88 | mp 152–154° (CHCl$_3$/n-hexane) pale yellow Crystals | 3390 1740 1700 | 1.05(3H,s), 1.23(3H,s), 2.45(3H,s), 3.60(1H,s), 3.81(3H,s), 4.77(1H,s), 4.8–5.1(1H,m), 7.4–8.3(4H,m) | C$_{18}$H$_{20}$N$_2$O$_7$ cal'd: 376.3679 found: 376.3683 |
| 8 (A-a) | (3-nitro group) R$^1$ = 1-(4-fluorobenzyl)-3-piperidyl group R$^2$ = methyl group | 75 | pale yellow oil | 3395 1745 1710 | As 1:1 isomeric mixture: 1.1–2.7(8H,m), 2.45 and 2.46 (total 6H, each s), 3.3–3.55 (2H,m), 3.59 and 3.60(total 2H, each s), 4.82(1H,s), 4.8–4.95(1H,m), 6.9–8.2(8H,m) | C$_{27}$H$_{28}$FN$_3$O$_7$ cal'd: 525.5366 found: 525.5371 |
| 9 (A-a) | (3-nitro group) R$^1$ = n-heptyl group R$^2$ = methyl group | 62 | pale yellow oil | 3400 1720 1705 | 0.85(3H,t,J=7Hz), 1.10–1.80(10H,m), 2.47(3H,s), 3.81(3H,s), 4.05(2H,t,J=7Hz), 4.78(1H,s), 7.42–8.30(4H,m) | C$_{22}$H$_{28}$N$_2$O$_7$ cal'd: 432.4757 found: 432.4759 |
| 10 (A-a) | (3-nitro group) R$^1$ = 2-phenyloxyethyl group R$^2$ = methyl group | 33 | pale yellow oil | 3400 1720 1710 | 2.47(3H,s), 3.79(3H,s) 3.90–4.30(2H,m), 4.30–4.60(2H,m), 4.79(1H,s), 6.75–8.30(9H,m) | C$_{23}$H$_{22}$N$_2$O$_8$ cal'd: 454.4389 found: 454.4391 |
| 11 (B) | (3-nitro group) R$^1$ = 2-(2-thienyl)ethyl group R$^2$ = methyl group | 26 | pale yellow oil | 3400 1720 1710 | 2.44(3H,s), 3.07(2H,t,J=6Hz), 3.80(3H,s), 4.20–4.40(2H,m), 4.77(1H,s), 6.68–8.20(7H,m) | C$_{21}$H$_{20}$N$_2$O$_7$S cal'd: 444.4654 found: 444.4656 |
| 12 (A-a) | (3-nitro group) R$^1$ = cyclopropylmethyl group R$^2$ = methyl group | 50 | pale yellow oil | 3400 1720 1710 | 0.10–0.25(2H,m), 0.40–0.60(2H,m), 0.95–1.10(1H,m), 2.48(3H,s), 3.82(3H,s), 3.90(2H,d,J=7Hz), 4.81(1H,brs), 7.45–8.20(4H,m) | C$_{19}$H$_{20}$N$_2$O$_7$ cal'd: 388.3791 found: 388.3789 |
| 13 (A-a) | (3-nitro group) R$^1$ = 2-(N—benzyl-N—methylamino)-1-phenylethyl group R$^2$ = methyl group | 11 | pale yellow oil | 3380 1710 | 2.02(3H,s), 2.45(3H,s), 2.40–2.75(2H,m), 3.28(1H,d,J=10Hz), 3.38(1H,d,J=10Hz), 3.76(3H,s), 4.93(1H,s), 5.97(1H,d,d,J= 8Hz, 5Hz), 6.98–8.20(14H,m) | C$_{31}$H$_{31}$N$_3$O$_7$ calc'd: 557.6065 found: 557.6064 |

TABLE A-continued

| Compound No. (Ref. Ex. No. showing method of synthesis) | Compound (position of nitro group) | Yield (%) | Description | IR Spectrum (cm$^{-1}$) as measured in CHCl$_3$ | NMR Spectrum (CDCl$_3$, 5 ppm, 270 MHz) | High-resolution mass spectrum |
|---|---|---|---|---|---|---|
| 14 (A-a) | (3-nitro group) R$^1$ = methoxyethyl group R$^2$ = methyl group | 98 | mp 135–136° (CHCl$_3$/n-hexane) colorless crystal | 3390 1740 1700 | 2.45(3H,s), 3.26(3H,s), 3.4–3.6(2H,m), 3.60(1H,s) 3.81(3H,s), 4.1–4.3(2H,m), 4.79(1H,s), 7.4–8.2(4H,m), 8.70(1H,s) | C$_{18}$H$_{20}$N$_2$O$_8$ cal'd: 392.3673 found: 392.3669 |
| 15 (A-b) | (2-nitro group) R$^1$ = 2-(morpholino)- ethyl group R$^2$ = ethyl group | 51 | pale yellow oil | 3400 1720 1705 | 1.31(3H,t,J=7Hz), 2.20–2.55(6H,m), 2.49(3H,s), 3.55(4H,t,J=5Hz), 4.00–4.35(4H,m), 5.17(1H,s), 7.22–8.00(4H,m) | C$_{22}$H$_{27}$N$_3$O$_8$ cal'd: 461.4739 found: 461.4741 |
| 16 (C) | (3-nitro group) R$^1$ = 8-pyrrolizydine- methyl group R$^2$ = methyl group | 82 | pale yellow oil | 3390 1740 1705 | 1.2–1.8(8H,m), 2.4–2.6(2H,m), 2.51(3H,s), 2.9–3.1(2H,m), 3.58(1H,s), 3.81(3H,s), 3.89(2H,s), 4.83(1H,s), 7.5–8.2(4H,m), 7.78(1H,brs) | C$_{23}$H$_{27}$N$_3$O$_7$ cal'd: 457.4857 found: 457.4862 |
| 17 (A-a) | (3-nitro group) R$^1$ = 2-(2-pyridyl)- ethyl group R$^2$ = methyl group | 85 | colorless oil | 3410 1750 1720 | 2.36(3H,s), 3.02(2H,t,J=6Hz), 3.52(1H,s), 3.78(3H,s), 4.49(2H,t,J=6Hz), 4.66(1H,s), 6.9–8.5(8H,m), 8.72(1H,brs) | C$_{22}$H$_{21}$N$_3$O$_7$ cal'd: 439.4271 found: 439.4273 |

EXAMPLE 1

5-[2-(4-Benzhydrylpiperazin-1-yl)ethyl]oxycarbonyl-2-chloro-3-methoxycarbonyl-6-methyl-4-(3-nitrophenyl)-1,4-dihydropyridine (Compound No. SUN 4752)

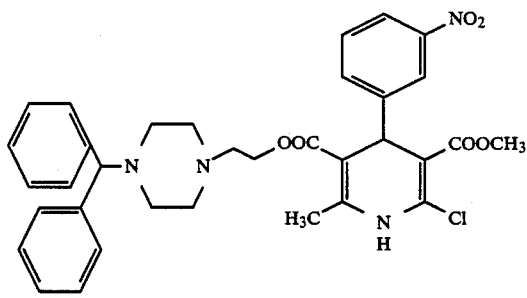

5-[2-(4-Benzhydrylpiperazin-1-yl)ethyl]oxycarbonyl-2-hydroxy-3-methoxycarbonyl-6-methyl-4-(3-nitrophenyl)-1,4-dihydropyridine (390 mg) was dissolved in phosphorus oxychloride (5 ml) and the mixture was heated under reflux for 3 hours and 10 minutes. After excess phosphorus oxychloride had been distilled off under reduced pressure, the reaction mixture was diluted with saturated potassium carbonate and subjected to extraction with chloroform. The extract was distilled off and the residue was subjected to silica gel column chromatography (elution solvent: 1% chloroform/methanol), thereby obtaining crude crystals. This crude crystals were recrystallized from a solution of chloroform/isopropylether/hexane to yield 210 mg (57.2%) of the desired compound.

EXAMPLE 2

2-Chloro-5-[1-(4-fluorobenzyl)piperidin-3-yl]oxycarbonyl-3-methoxycarbonyl-6-methyl-4-(3-nitrophenyl)-1,4-dihydroppyridine (Compound No. SUN 5142)

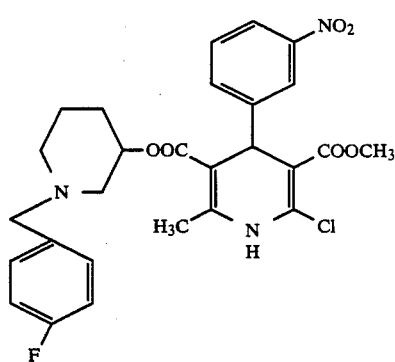

5-[1-(4-fluorobenzyl)piperidin-3-yl]oxycarbonyl-2-hydroxy-3-methoxycarbonyl-6-methyl-4-(3-nitrophenyl)-1,4-dihydropyridine (1.85 g) was dissolved in phosphorus oxychloride (22 ml) and the mixture was heated under reflux for 3 hours. After excess phosphorus oxychloride had been distilled off under reduced pressure, the reaction mixture was diluted with saturated potassium carbonate and subjected to extraction with chloroform. The extract was distilled off and the residue was subjected to silica gel column chromatography (elution solvent: 0.7–2.5% chloroform/methanol) and to alumina column chromatography (elution solvent: chloroform/hexane=3/2), so as to obtain 0.98 g (51.3%) of the desired compound.

The physicochemical data of SUN 4752 and SUN 5142 are shown in Table 1.

Additional compounds were synthesized by repeating Examples 1 and 2 and their physicochemical data are shown in Table 1 together with the respective compound numbers.

TABLE 1

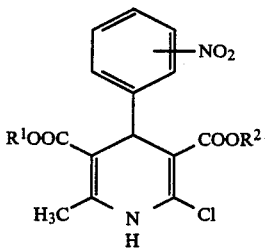

| Compound No. (Ref. Ex. No. showing method of synthesis) | Compound (position of nitro group) | Yield (%) | Description | IR Spectrum ($cm^{-1}$) as measured in $CHCl_3$ | NMR Spectrum ($CDCl_3$, 5 ppm, 270 MHz) | High-resolution mass spectrum |
| --- | --- | --- | --- | --- | --- | --- |
| SUN 4616 | (3-nitro group) $R^1$ = methyl group $R^2$ = methyl group | 44 | mp 225–228° ($CHCl_3$/n-hexane) pale yellow crystals | 3420 1700 | 2.40(3H,s), 3.66(1H,s), 3.70(3H,s), 5.25(1H,s), 6.08(1H,s), 7.39–8.12(4H,m) | $C_{16}H_{15}ClN_2O_6$ cal'd: 574.0566 found: 574.0561 |
| SUN 4671 | (2-nitro group) $R^1$ = methyl group $R^2$ = methyl group | 6 | mp 162–164° ($CHCl_3$/n-hexane) pale yellow crystals | 3425 1700 | 2.36(3H,s), 3.60(3H,s) 3.65(3H,s), 5.87(1H,s), 5.95(1H,s), 7.28–7.73(4H,m) | $C_{16}H_{15}ClN_2O_6$ cal'd: 574.0566 found: 574.0570 |
| SUN 4752 | (3-nitro group) $R^1$ = 2-(4-benzhydryl-1-piperazinyl)ethyl group $R^2$ = methyl group | 57 | mp 131–134° ($CHCl_3$/ isopropylether/ n-hexane) pale yellow crystals | 3425 1700 | 2.3–2.6(8H,m), 2.38(3H,s), 2.5–2.7(2H,m), 3.67(3H,s), 4.1–4.2(2H,m), 4.19(1H,s), 5.23(1H,s), 6.07(1H,s), 7.1–8.1(14H,m) | $C_{34}H_{35}ClN_4O_6$ cal'd: 631.1318 found: 631.1324 |
| SUN 5017 | (3-nitro group) $R^1$ = 2-(N—benzyl-N—methylamino)ethyl group $R^2$ = methyl group | 14 | pale yellow oil | 3425 1700 | 2.20(3H,s), 2.37(3H,s), 2.5–2.7(2H,m), 3.50(1H,s), 3.69(3H,s), 4.18(2H,t,J=6Hz), 5.27(1H,s), 6.27(1H,s), 7.2–8.2(9H,m), | $C_{25}H_{26}ClN_3O_6$ cal'd: 499.9537 found: 499.9532 |
| SUN 5018 | (3-nitro group) $R^1$ = 2-[4-(9-fluorenyl)-1-piperazinyl]ethyl group $R^2$ = methyl group | 33 | pale yellow powder (mp 110–150°) | 3425 1700 | 2.3–2.7(10H,m), 2.35(3H,s), 3.65(3H,s), 4.05–4.25(2H,m), 4.82(1H,s), 5.22(1H,s), 6.39(1H,s), 7.2–8.2(12H,m) | $C_{34}H_{33}ClN_4O_6$ cal'd: 629.1160 found: 629.1156 |
| SUN 5088 | (3-nitro group) $R^1$ = 5-phenylpentyl group $R^2$ = methyl group | 48 | pale yellow oil | 3420 1710 1695 | 1.40–1.80(6H,m), 2.37(3H,s), 2.56(2H,t,J=7Hz), 3.70(3H,s), 3.70(2H,t,J=7Hz), 5.23(1H,s), 7.10–8.30(9H,m) | $C_{26}H_{27}ClN_2O_6$ cal'd: 498.9660 found: 498.9659 |
| SUN 5141 | (3-nitro group) $R^1$ = isopropyl group $R^2$ = methyl group | 11 | mp 161–165° ($CHCl_3$/ether/ n-hexane) colorless crystals | 3430 1700 | 1.10(3H,d,J=6.5Hz), 1.26(3H,d,J=6.5Hz), 2.38(3H,s), 3.70(3H,s), 4.97(1H,quintet,J=6Hz), 5.22(1H,s), 6.30(1H,s), 7.4–8.1(4H,m) | $C_{18}H_{19}ClN_2O_6$ cal'd: 394.8136 found: 394.8142 |
| SUN 5142 | (3-nitro group) $R^1$ = 1-(4-fluorobenzyl)-3-piperidyl group $R^2$ = methyl group | 51 | colorless powder | 3450 1700 | As 1:1 isomeric mixture: 1.2–2.8(8H,m), 2.36(3H,s), 3.3–3.65(2H,m), 3.71 and 3.72(total 6H, each s), 4.7–4.9(1H,m), 5.23(1H,s), 6.37(1H,s), 6.9–8.2(8H,m) | $C_{27}H_{27}ClN_3O_6$ cal'd: 543.9823 found: 543.9819 |
| SUN 5143 | (3-nitro group) $R^1$ = n-heptyl group $R^2$ = methyl group | 30 | pale yellow powder | 3400 1700 1695 | 0.87(3H,t,J=7Hz), 1.15–1.75(10H,m), 2.40(3H,s), 3.71(3H,s), 3.98–4.24(2H,m), 5.25(1H,s), 7.42(1H,t,J=8Hz), 7.65(1H,d,J=8Hz), 8.04(1H,d,J=8Hz), 8.14(1H,s) | $C_{22}H_{27}ClN_2O_6$ cal'd: 450.9214 found: 450.9220 |
| SUN 5151 | (3-nitro group) $R^1$ = 2-phenyloxyethyl group $R^2$ = methyl group | 8 | pale yellow oil | 3420 1705 | 2.40(3H,s), 3.68(3H,s), 4.05–4.20(2H,m), 4.30–4.55(2H,m), 5.25(1H,s), 6.80–8.15(9H,m) | $C_{23}H_{21}ClN_2O_6$ cal'd: 472.8846 found: 472.8851 |
| SUN 5163 | (3-nitro group) $R^2$ = 2-(2-thienyl)ethyl group $R^2$ = methyl group | 9 | pale yellow oil | 3430 1710 1700 | 2.36(3H,s), 3.12(2H,t,J=6Hz), 3.71(3H,s), 4.31(2H,t,J=6Hz), 5.24(1H,s), 6.76–8.20(7H,m) | $C_{21}H_{19}ClN_2O_6S$ cal'd: 462.9111 found: 462.9108 |
| SUN 5164 | (3-nitro group) $R^1$ = cyclopropylmethyl | 5 | pale yellow oil | 3440 1715 | 0.10–0.30(2H,m), 0.50–0.60(2H,m), | $C_{19}H_{19}ClN_2O_6$ cal'd: 654.1867 |

TABLE 1-continued

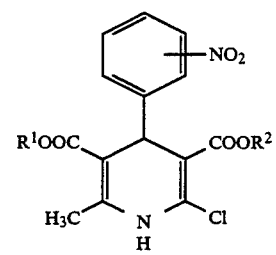

| Compound No. (Ref. Ex. No. showing method of synthesis) | Compound (position of nitro group) | Yield (%) | Description | IR Spectrum (cm$^{-1}$) as measured in CHCl$_3$ | NMR Spectrum (CDCl$_3$, δ ppm, 270 MHz) | High-resolution mass spectrum |
|---|---|---|---|---|---|---|
| | group R$^2$ = methyl group | | | 1705 | 1.00–1.18(1H,m), 2.40(3H,s), 3.70(3H,s), 5.27(1H,s), 7.38–8.24(4H,m) | found: 654.1866 |
| SUN 5181 | (3-nitro group) R$^1$ = 2-(N—benzyl-N—methylamino)-1-phenylethyl group R$^2$ = methyl group | 39 | pale yellow oil | 3430 1710 1700 | 2.08(3H,s), 2.36(3H,s), 2.55–2.78(2H,m), 3.33(1H,d,J=10Hz), 3.40(1H,d,J=10Hz), 3.71(3H,s), 5.32(1H,s), 5.99(1H,m), 7.00–8.25(14H,m) | C$_{31}$H$_{30}$ClN$_3$O$_6$ cal'd: 576.0522 found: 576.0526 |
| SUN 5220 | (3-nitro group) R$^1$ = meythoxyethyl group R$^2$ = methyl group | 2 | pale yellow oil | 3440 1710 | 2.39(3H,s), 3.34(3H,s), 3.5–3.6(2H,m), 3.69(3H,s), 4.1–4.3(2H,m), 5.26(1H,s), 6.31(1H,s), 7.3–8.2(4H,m) | C$_{18}$H$_{19}$ClN$_2$O$_7$ cal'd: 410.8130 found: 410.8135 |
| SUN 5252 | (2-nitro group) R$^1$ = 2-(morpholino)-ethyl group R$^2$ = ethyl group | 16 | pale yellow oil | 3430 1705 1700 | 1.19(3H,t,J=7Hz), 2.35(3H,s), 2.20–2.60(6H,m), 3.61(4H,t,J=5Hz), 4.00–4.30(4H,m), 5.95(1H,s) 7.25–7.80(4H,m) | C$_{22}$H$_{26}$ClN$_3$O$_7$ cal'd: 479.9196 found: 479.9201 |
| SUN 5334 | (3-nitro group) R$^1$ = 8-pyrrolizydine-methyl group R$^2$ = methyl group | 8 | pale yellow oil | 3425 1700 | 1.2–1.9(8H,m), 2.43(3H,s), 2.5–2.7(2H,m), 2.9–3.1(2H,m), 3.72(3H,s), 3.80(2H,s), 5.29(1H,s), 6.15(1H,brs), 7.4–8.2(4H,m) | C$_{23}$H$_{26}$ClN$_3$O$_6$ cal'd: 475.9314 found: 475.9309 |
| SUN 5336 | (3-nitro group) R$^1$ = 2-(2-pyridyl)ethyl group R$^2$ = methyl group | 59 | pale yellow crystals (CHCl$_3$/n-hexane) mp 114–116° | 3440 1705 | 2.30(3H,s), 3.10(2H,t,J= 6.5Hz), 3.69(3H,s) 4.49(2H,t,J=6.5Hz), 5.15(1H,s), 7.1–8.6(8H,m) | C$_{22}$H$_{20}$ClN$_3$O$_6$ cal'd: 457.8728 found: 457.8733 |

EXAMPLE 3

The coronary vascular dilative effect of selected 2-chloro-1,4-dihydropyridine derivatives of the present invention was tested.

Test method:

Hartley guinea pigs (weight 400–500 g) were killed by a blow on the head and their hearts were immediately isolated. The hearts were perfused with Krebs-Henseleit solution bubbled with a mixture of 95% $O_2$+5% $CO_2$ and maintained at 37° C. at a constant rate of 6 ml/minute according to Langendorff's method [J. Pharmacol. Methods 2, 143 (1979)]. The perfusion pressure was measured continuously by a pressure transducer. Samples were prepared by emulsifying 1 mg of a test compound in 1 ml of a mixture of dimethylsulfoxide and physiological saline solution (1:9) and diluting with physiological saline solution to the predetermined concentration. 0.1 ml of the diluted solution was administered into the coronary artery via rubber tube connected to an aorta cannula to obtain ED$_{50}$ (μg/heart) data as shown in Table 2. The numbers of the compounds in the Table correspond respectively to those of the working examples described above.

TABLE 2

| Compound No. | ED$_{50}$ (μg/heart) |
|---|---|
| SUN 5141 | 0.05 |
| SUN 5142 | 0.03 |
| SUN 5143 | 0.02 |

EXAMPLE 4

The pharmacological effect (ED$_{30}$) of selected 2-chloro-1,4-dihydropyridine derivatives of the present invention with respect to the vascular resistance of the vertebral artery in anesthetized dogs was treated by the following procedures.

Test Method:

Adult dogs of either sex (7–14 kg in body weight) were anesthetized with at first thiopental sodium (35 mg/kg, intraperitoneal), anesthetized with urethane (400 mg/kg, intravenous) and α-chloalose (60 mg/kg, intravenous) and kept under artificial respiration throughout the experiment. After thoracotomy at the left first intercostal space, the vertebral artery was exposed and blood flow was measured with an intracorporeal flow probe connected to an electromagnetic flowmeter (MF-27, Nihon Kohden).

At the same time, continuous measurement of the following parameters was made: systemic blood pressure (mean pressure) at the right femoral artery, the limb lead II ECG, the heart rate with a tachometer triggered by the R wave of ECG, and the vascular resistance determined by loading an electronic divider (EO-601 G, Nihon Kohden) with the mean values of blood pressure and vertebral artery blood flow. All of these parameters were recorded simultaneously on a polygraph (RM-600, Nihon Kohden).

All the test compounds were injected through a cannula inserted into the femoral vein.

The $ED_{30}$ ($\mu$g/kg) values obtained by intravenous injection and the values of $T_{\frac{1}{2}}$ (min) (the time to reach 50% of the resistance drop) are shown in Table 3, wherein the Compound Numbers are keyed to the Example Numbers.

TABLE 3

| Compound No. | $ED_{30}$ ($\mu$g/kg) | $T_{\frac{1}{2}}$ (min) |
| --- | --- | --- |
| SUN 4616 | 1.2 | — |
| SUN 4671 | 0.59 | — |
| SUN 4752 | 3.0 | >30 |
| SUN 5017 | 3.3 | 17.0 |
| SUN 5018 | 4.3 | 15.5 |
| SUN 5088 | 1.4 | 17.0 |
| SUN 5141 | 0.28 | 10.6 |
| SUN 5142 | 2.8 | >30 |
| SUN 5143 | 2.2 | 20.5 |
| SUN 5151 | 3.6 | 10.5 |
| SUN 5163 | 9.3 | 14.0 |
| SUN 5164 | 0.22 | — |
| SUN 5181 | 2.1 | — |
| SUN 5220 | 5.8 | 13.5 |
| SUN 5252 | 3.6 | — |

EXAMPLE 5

Selected compounds of the present invention were tested for their hypotensive action in conscious spontaneously hypertensive rats (SHR).

Test method:

A group of 17 to 20-week old male SHR were anesthetized with ether and a cannula was inserted into the left femoral artery. At least one day after the operation, the cannula was connected to a pressure transducer and the blood pressure was measured continuously under conscious and unrestrained condition, thereby obtaining the data shown in Table 4. Each of the test compounds as a clear suspension in 0.5% CMC-Na was administered orally at a dose of 10 mg/kg (body weight) to each animal which was starved overnight.

TABLE 4

| Compound No. | Blood pressure drop (%) | |
| --- | --- | --- |
| | Maximum drop | 6 hours |
| SUN 4752 | 35 | 30 |
| SUN 5141 | 51 | 33 |
| Nicardipine | 39 | 10-20 |

EXAMPLE 6

The acute toxicity ($LD_{50}$) data of selected compounds of the present invention as administered to two groups of male mice were obtained and the results are shown in Table 5. One group of mice which received peroral administration had been starved overnight. Each of the test compounds was suspended in 0.5% CMC-Na for peroral administration, or dissolved in dimethyl sulfoxide and diluted with physiological saline solution for intravenous injection.

TABLE 5

| Compound No. | $LD_{50}$ (mg/kg) | |
| --- | --- | --- |
| | i.v. | p.o. |
| SUN 4752 | 23-27 | 1000 |
| SUN 5141 | 80 | — |
| Nicardipine | 12.2 | 455 |

The compounds of this invention have a strong and long-lasting vasodilative effect. Therefore, said compounds are considered to be useful as agents for causing coronary vascular dilation or treating hypertension or disturbances of cerebral circulation. Such disorders can be treated by administering the compound of the present invention, at a low dose level and at infrequent interval. This will make sure that the intended treatment can be done safely and easily.

We claim:

1. A novel 1,4-dihydropyridine derivative of the formula (1):

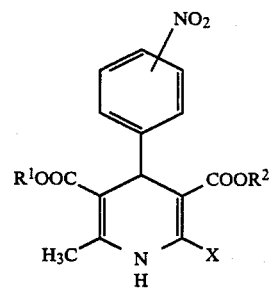

wherein X is a halogen; $R^1$ is
a straight or branched alkyl group having 1 to 10 carbon atoms,
the group —$(CH_2)_n$—Y, where n is an integer of 0 to 8, provided that when n is zero or 1, —$(CH_2)n$— is not bonded to the hetero atom of Y; Y is a cyclic alkyl group having 3-6 carbon atoms, an aryl group having 6-10 carbon atoms, a thienyl group, a pyridyl group, a morpholinyl group or a pyrrolizidinyl group, the group

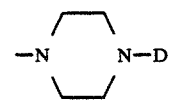

(where D is an aryl or aralkyl group having 6-15 carbon atoms), or a 3-piperidinyl group substituted by a phenylalkyl group of 7-10 carbon atoms which may be substituted by one or two halogens,
the group —$(CH_2)_m$—O—Z where m is an integer of 1 to 8 and Z is $C_1$-$C_5$ alkyl or $C_6$-$C_{10}$ aryl group, or the group

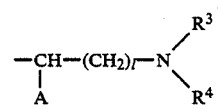

(where l is an integer of 1-7; A is a hydrogen atom or $C_6$-$C_{10}$ aryl group; and $R^3$ and $R^4$ which may be the same or different represent an $C_1$-$C_5$ alkyl, $C_6$-$C_{10}$ aryl or aralkyl group); and $R^2$ is $C_1$-$C_3$ alkyl group, or a pharmaceutically acceptable acid addition salt thereof.

2. A compound according to claim 1 wherein $R^1$ is the group $-(CH_2)_n-Y$ where n is 1 or 2, and Y is a cyclopropyl or cyclopentyl group.

3. A compound according to claim 1 wherein n is an integer of 2 to 4.

4. A compound according to claim 1 wherein m is an integer of 1 to 4.

5. A compound according to claim 1 wherein X is a chlorine atom.

6. A vasodilative composition which contains an effective amount of a novel 1,4-dihydropyridine derivative of the formula (1):

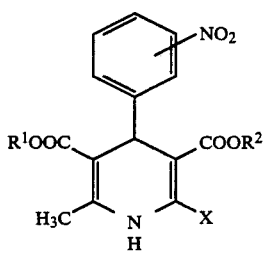
(1)

wherein X is a halogen; $R^1$ is
a straight or branched alkyl group having 1 to 10 carbon atoms,
the group $-(CH_2)_n-Y$, wherein n is an integer of 0 to 8, provided that when n is zero or 1, $-(CH_2)n-$ is not bonded to the hetero atom of Y; Y is a cyclic alkyl group having 3-6 carbon atoms, an aryl group having 6-10 carbon atoms, a thienyl group, a pyridyl group, a morpholinyl group or a pyrrolizidinyl group, the group

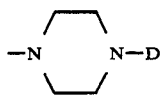

(where D is an aryl or aralkyl group having 6-15 carbon atoms), or a 3-piperidinyl group substituted by a phenylalkyl group of 7-10 carbon atoms which may be substituted by one or two halogens, the group $-(CH_2)_m-O-Z$ where m is an integer of 1 to 8 and Z is $C_1-C_5$ alkyl or $C_6-C_{10}$ aryl group, or the group,

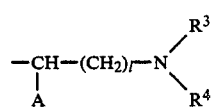

(where l is an integer of 1-7; A is a hydrogen atom, or $C_6-C_{10}$ aryl group; and $R^3$ and $R^4$ which may be the same or different represent an $C_1-C_5$ alkyl, $C_6-C_{10}$ aryl or aralkyl group); and $R^2$ is $C_1-C_3$ alkyl group, or a pharmaceutically acceptable acid additional salt thereof.

* * * * *